United States Patent [19]

Baldwin et al.

[11] 4,408,047
[45] Oct. 4, 1983

[54] IMIDAZODIAZINES

[75] Inventors: John J. Baldwin, Lansdale; William C. Lumma, Jr., Pennsburg, both of Pa.

[73] Assignee: Merck & Co., Inc., Rahway, N.J.

[21] Appl. No.: 322,796

[22] Filed: Nov. 19, 1981

Related U.S. Application Data

[62] Division of Ser. No. 135,022, Mar. 28, 1980, Pat. No. 4,330,543, which is a division of Ser. No. 969,631, Dec. 14, 1978, Pat. No. 4,233,301, which is a division of Ser. No. 796,958, May 16, 1977, Pat. No. 4,166,851.

[51] Int. Cl.$^3$ .................. C07D 487/04; C07D 487/14
[52] U.S. Cl. .................................... 544/250; 544/281; 544/117; 544/115; 544/80
[58] Field of Search ............... 544/281, 250, 117, 115, 544/80

[56] References Cited

U.S. PATENT DOCUMENTS 4,153,695  5/1979  Turner .............................. 544/281
4,178,449  12/1979  Dusza et al. ..................... 544/281

FOREIGN PATENT DOCUMENTS 2362331  6/1974  Fed. Rep. of Germany ...... 544/281
2511316  9/1975  Fed. Rep. of Germany ...... 544/281

Primary Examiner—John M. Ford
Attorney, Agent, or Firm—Salvatore C. Mitri; Daniel T. Szura

[57] ABSTRACT

Novel imidazopyridines, -pyrazines, -pyrimidines and -pyridazines having a 3-amino-2-OR-propoxy substituent, are disclosed. The compounds have $\beta$-adrenergic blocking activity.

7 Claims, No Drawings

IMIDAZODIAZINES

This is a division of application Ser. No. 135,022, filed Mar. 28, 1980, now U.S. Pat. No. 4,330,543, which in turn is a divisional application of Ser. No. 969,631, filed Dec. 14, 1978, now U.S. Pat. No. 4,233,301, which in turn is a division of U.S. application Ser. No. 796,958, filed May 16, 1977, now U.S. Pat. No. 4,166,851, issued Sept. 4, 1979.

BACKGROUND OF THE INVENTION

The present invention involves imidazoazine and diazine compounds having an 3-amino-2-OR-propoxy substituent. The compounds have pharmacological activity exemplified by β-adrenergic blockade.

Condensed ring hetero cyclic compounds having an aminohydroxypropoxy substituent are known as β-adrenergic blocking agents [Crowther et al., J. Med. Chem., 260–266 (1972)].

It has now been discovered that certain novel 3-amino-2-OR-propoxy substituted imidazoazines and imidazodiazines have pharmaceutical activity including β-adrenergic blockade.

SUMMARY OF THE INVENTION

Imidazopyridines, imidazopyrimidines, imidazopyrazines and imidazopyridazines having a 3-amino-2-OR-propoxy substituent and their pharmaceutical use.

DESCRIPTION OF THE PREFERRED EMBODIMENTS

An embodiment of this invention is compounds having the formula

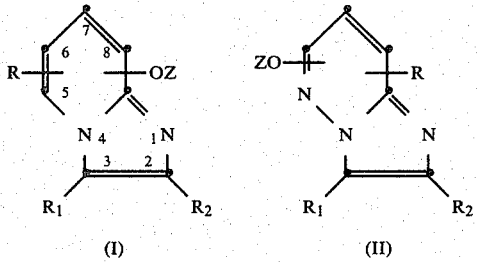

(I)    (II)

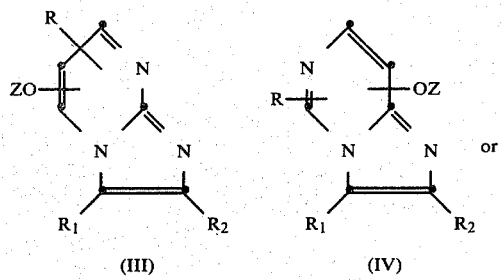

(III)    (IV)

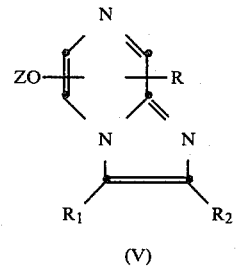

(V)

and pharmaceutically acceptable salts thereof wherein
Z is —$CH_2$—CH O$R_3$—$CH_2$—NH$R_4$ wherein $R_3$ is H or $C_2$-$C_{12}$ acyl and $R_4$ is $C_1$-$C_{12}$alkyl, R is H, —$SCF_3$, —CN, halogen, $C_{1-6}$alkyl, $NH_2$, $C_1$-$C_6$ haloalkyl, $C_1$-$C_{12}$acyl, phenyl, —COO$R_5$ wherein $R_5$ is H,$C_1$-$C_6$alkyl or $C_6$-$C_{12}$ carbocyclic aryl, —CON$R_6R_7$ wherein $R_6$ and $R_7$ when separate, are H or $C_1$-$C_6$alkyl and when joined, are —$CH_2$—($CH_2$)$_3$—$CH_2$, —$CH_2$—$CH_2$—O—$CH_2$—$CH_2$—, —$CH_2$—$CH_2$—NH—$CH_2$—$CH_2$—, or —$CH_2$—$CH_2$—N($CH_3$)—$CH_2$—$CH_2$—, $C_1$-$C_6$alkylthio, $C_1$-$C_6$ alkylsulfinyl or $C_1$-$C_6$alkylsulfonyl, and $R_1$ and $R_2$ when separate are R and when joined are —($CH_2$)$_n$— wherein n is 3,4 or 5.

The ring positions are numbered as shown within Formula I.

The pharmaceutically acceptable salts are the acid addition salts of the formula I—V free bases. Suitable acids include organic as well as inorganic acids. Examples of useful organic acids are carboxylic acids such as acetic acid, pamoic acid, maleic acid, succinic acid, citric acid, tartaric acid, oxalic acid, malic acid, pivalic acid, heptanoic acid, lauric acid, propanoic acid, pelargonic acid, oleic acid and the like, and non-carboxylic acids such as isethionic acid. Examples of useful inorganic acids are the hydrogen halides i.e. HCl, HBr, HI, phosphoric acid, sulfuric acid, and the like. The hydrohalide salts, especially the hydrochlorides and maleic acid salts, especially the hydrogen maleate, are preferred.

Suitable R, $R_1$ and $R_2$ (when separate) substituents include H, $NH_2$,$SCF_3$, phenyl, cyano, halogen e.g., Cl, Br, I or F, $C_1$-$C_6$alkyl e.g., methyl, t-butyl, isoamyl, n-hexyl and the like; halo- $C_{1-6}$alkyl such as ω-chlorohexyl, bromopropyl; 1,2-dibromoethyl, 2,3-dichlorobutyl, —$CF_3$, —$CBr_3$, —$CH_2F$, —$CHCl_2$ and the like; $C_{1-12}$acyl of the formula

wherein L is H, alkyl e.g., $CH_3$, undecyl, isobutyl, 5-ethyl-n-pentyl, ethyl or aryl e.g., phenyl,

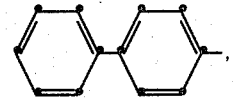

naphthyl, indanyl, p-tolyl and the like; the carboxy group and ester and amide derivatives thereof, the $C_1$-$C_6$alkylthio, sulfinyl and sulfonyl derivatives thereof. The ester groups are $C_1$-$C_6$-alkylester exemplified by —COOCH$_3$, —COOC$_6$H$_{13}$, —COOCH(CH$_3$)$_2$, —COOC$_2$H$_5$ and the like and $C_6$$C_{12}$ arylester, preferably carbocyclic aryl, exemplified by C$_6$H$_5$—OOC, p—CH$_3$—C$_6$H$_4$—OOC—, C$_6$H$_5$—C$_6$H$_4$—OOC—, C$_{10}$H$_7$—OOC— and the like. The amide groups include —CONH$_2$, $C_1$-$C_6$ substituted amide groups such as —CON(CH$_3$)$_2$, —CON(C$_6$H$_{13}$)$_2$, —CONHC$_2$H$_5$, —CON (sec. butyl)$_2$ and the like and carbonyl heterocyclic groups such as

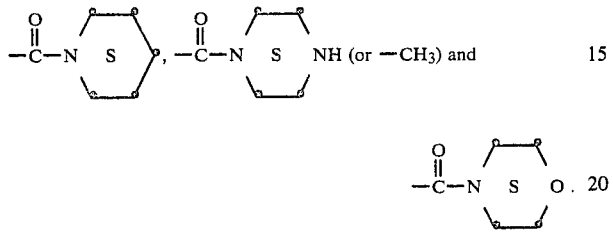

The $C_1$-$C_6$ alkyl-thio, -sulfinyl and -sulfonyl groups are exemplified by CH$_3$—S—, C$_6$H$_{13}$—S, (CH$_3$)$_3$C—S—, (CH$_3$)$_2$CH—SO—, CH$_3$—SO$_2$—, C$_2$H$_5$—SO$_2$, C$_6$H$_{13}$—SO; C$_5$H$_{11}$—SO—, sec.-butyl-SO$_2$ and the like. The preferred R, R$_1$ and R$_2$ (when separate) groups are hydrogen, haloalkyl, especially CF$_3$, cyano, alkyl especially methyl, halogen especially Cl and Br, alkylthio especially —SCH$_3$ and phenyl.

R$_1$ and R$_2$ may also be joined forming the alkylene group —(CH$_2$)$_n$— where n is 3, 4 or 5 preferably 3 or 4 and more preferably 4.

R$_3$ may be hydrogen or C$_{2-12}$acyl, The C$_{2-12}$acyl groups include alkanoyl groups such as acetyl, pivaloyl, dodecanoyl, hexanoyl, succinoyl and the like—and carbocyclic aroyl groups such as benzoyl, 1- or 2-naphthoyl, p-methylbenzoyl, p-phenylbenzoyl and the like. The C$_2$-C$_6$ alkanoyl and benzoyl groups are preferred acyl groups. Compounds where R$_3$ is hydrogen are preferred.

The R$_4$ substituent includes C$_1$-C$_{12}$alkyl groups and preferably the C$_1$-C$_6$alkyl groups. The alkyl groups are exemplified by methyl, C$_{12}$H$_{25}$—, hexyl, 2-ethylhexyl, isopropyl, sec-butyl, heptyl and the like. The C$_{3-4}$ branched chain alkyl R$_4$ groups are more preferred, with t-butyl being a most preferred group.

The present imidazo compounds have one chiral center which confers optical activity. The optical isomers are designated conventionally as L and D, l and d, + and −, S and R or by combinations of these symbols. Where the formula or compound name herein carries no specific designation, the formula or name includes the individual isomers, the mixtures thereof and racemates.

The imidazo compounds of Formula I–V where R is H, phenyl, cyano or CF$_3$, R$_1$ and R$_2$ are halogen, alkyl, —SCF$_3$ or said alkylene groups, R$_3$ is H and R$_4$ is C$_{3-4}$ branched alkyl, especially t-butyl, are preferred. The compounds where R is cyano are particularily preferred, especially when the cyano group is ortho to the —OZ moiety.

Preferred compounds are the imidazopyridines of Formulae I and II, and especially those having the formula

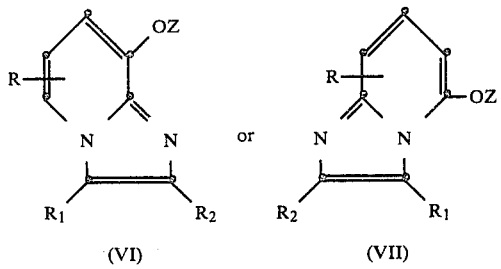

More preferred VI and VII compounds have the R group ortho to the —OZ group. Most preferred compounds have R$_3$=H and R$_4$=t-butyl.

Especially preferred imidazopyridines have the formula

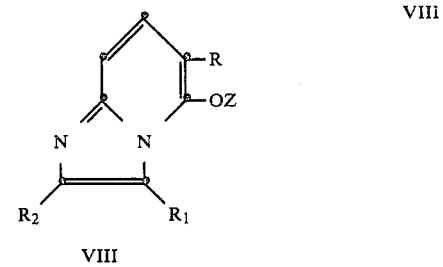

VIII

Compounds of formula VIII where R is H or CN, R$_1$ and R$_2$ and H, Cl or C$_1$-C$_6$alkyl, —SCF$_3$ or joined as —(CH$_2$)$_3$ or —(CH$_2$)$_4$ are more preferred and where R is hydrogen, R$_3$ is hydrogen and R$_4$ is C$_3$-C$_4$ branched alkyl, especially t-butyl, the compounds are particularily preferred.

Other preferred compounds are the imidazopyridines of formula V and especially those having the formula

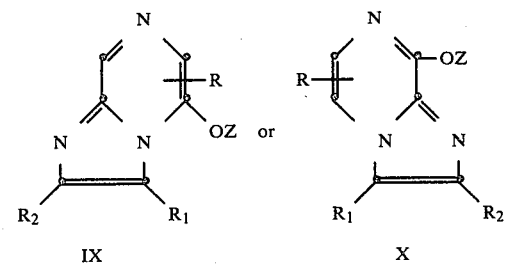

Preferred R is H or CN. Preferred R$_1$ and R$_2$ are H, C$_1$-C$_6$-alkyl, —SCF$_3$ or Cl or joined as —(CH$_2$)$_3$-4. Preferred R$_3$ is H and R$_4$ is C$_3$-C$_4$alkyl, especially t-butyl.

The imidazo compounds of the present invention may be prepared by any convenient process.

One such process involves the coupling of an imidazoazine or diazine with a suitable substituted oxazolidine and hydrolyzing the reaction product obtained. This process is illustrated by the following set of reaction equations:

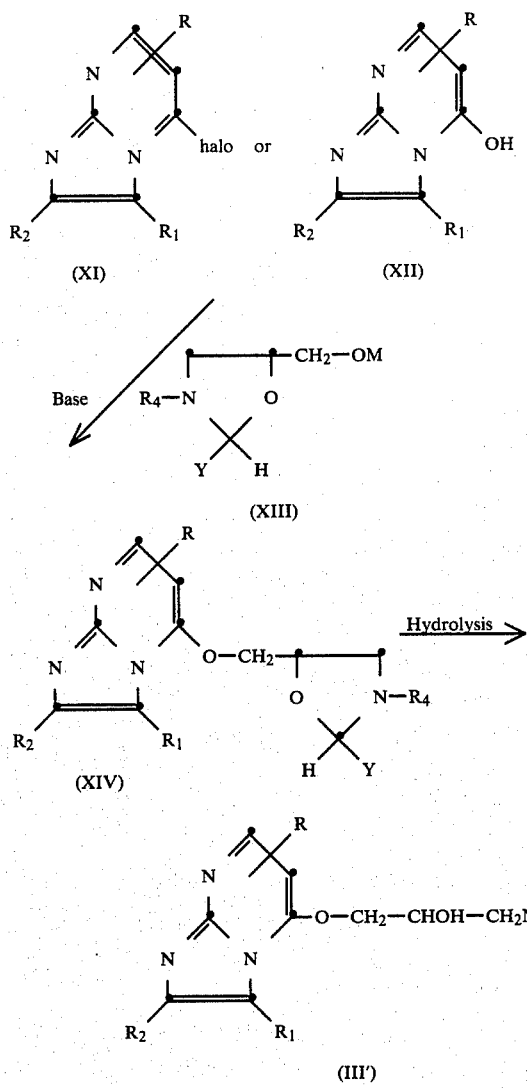

Halo may be Cl, Br and I, with Cl being preferred. M is H or alkali metal when XI is the reactant while M is an aryl or alkylsulfonyl group when XII is the reactant. Suitable bases are exemplified by $K_2CO_3$, NaH, K—O—C(CH$_3$)$_3$, organic lithium such as n-butyllithium, phenyllithium, lithium diisopropyl amide etc. Y is hydrogen or a $C_1$-$C_{12}$alkyl or $C_6$-$C_{12}$aryl residue of any suitable aldehyde

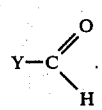

Examples of such aldehydes are arylaldehydes such as benzaldehyde, naphthaldehyde, 4-phenylbenzaldehyde, tolualdehyde, nitrobenzaldehyde and the like, or alkanals such as acetaldehyde, butyraldehyde,

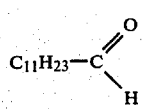

and the like. The process for preparing oxazolidines (XIII; M=H) is disclosed in U.S. Pat. No. 3,718,647 and U.S. Pat. No. 3,657,237 and to the extent necessary the pertinent disclosure is incorporated herein by reference. If it is desired to use alkali metal salt of the oxazolidine, it may be prepared in a conventional manner by reaction of the corresponding hydroxymethyloxazolidine with an appropriate amount of a suitable alkali metal base.

The coupling reaction can be carried out at temperatures ranging from about 0° to about 100° C. A temperature range of about 10° to about 50° is preferred. The reaction is generally carried out in a solvent. Any suitable solvent may be used. Examples of useful solvents are dioxane, toluene, tetrahydrofuran, dimethylformamide, dimethylsulfoxide, hexamethylphosphormaide, tert. butanol and the like. The hydrolysis is carried out using conventional acid hydrolysis reagents and techniques e.g. treatment with a solution of any suitable acid such as $CH_3COOH$, HCl or $H_2SO_4$. The hydrolysis product can be directly obtained as the salt of the acid used for the hydrolysis. Ordinarily, the product is recovered as the free base after conventional neutralization of the salt.

The coupling reaction is ordinarily carried out at atmospheric pressure. Higher pressures may be used if desired.

When a racemic oxazolidine (Formula XIII) is used as a reactant, the product is obtained as a racemate. The racemate may be separated into its individual enantiomers by conventional resolution techniques.

When $R_4$ in the oxazolidine (Formula XIII or XIV) is other than hydrogen, in addition to the chiral center at oxazolidine position 5 there is a second chiral center at position 2. However, whenever the oxazolidine is designated e.g. as (S), (R) or (R,S), this designation refers only to the optical configuration around the carbon atom at the 5 position.

By using a single optical isomer of said oxazolidine in the above reactions, the product may be obtained directly as a single enantiomer. Thus, if the S-isomer of the oxazolidine is used, then the product obtained will be the S-isomer. This provides a convenient way for directly preparing individual isomers of the present pyridines.

Imidazoazines and diazines of the present invention wherein $R_3$ is other than hydrogen are conveniently prepared by treating the corresponding compound where $R_3$ is hydrogen with an appropriate acylating agent such as an acyl halide, e.g. undecanoyl chloride, pivaloyl chloride, benzoychloride, p-methoxybenzoyl chloride, an anhydride e.g. acetic anhydride, and the like. The reaction is illustrated by the following equation:

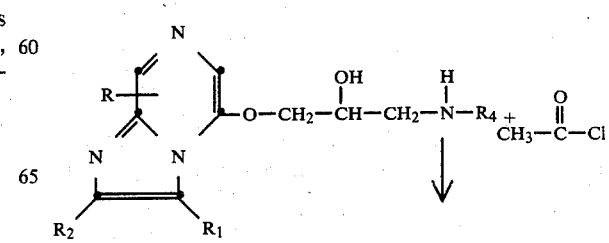

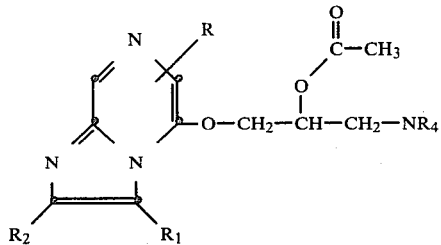

The compounds of the present invention also include the pharmaceutically acceptable salt of the novel imidazoazine or diazine. These salts are conveniently prepared e.g. by treating the imidazo compound with an appropriate amount of a useful acid, generally in a suitable solvent.

Another process for preparing the imidazo compounds having a cyano substituent is by halogen displacement as illustrated by the following equation:

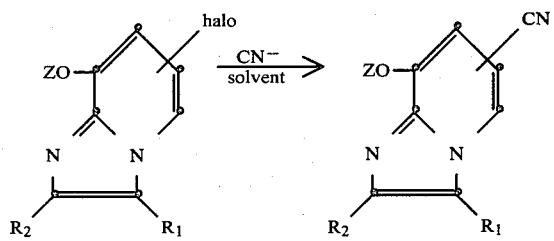

The CN⁻ supplying reagent may be any suitable metal salt such as CuCN, AgCN etc. Solvents which may be used are examplified by dimethylformamide, pyridine, 2,4-lutidine and the like. The reaction is generally carried out at elevated temperature, preferably in the 100°–180° C. range.

Additional processes for preparing imidazo compounds with certain other substituents are illustrated by the following equation sequences. Conventional reaction conditions are employed. The desired other substituent is underlined.

Sequence 1

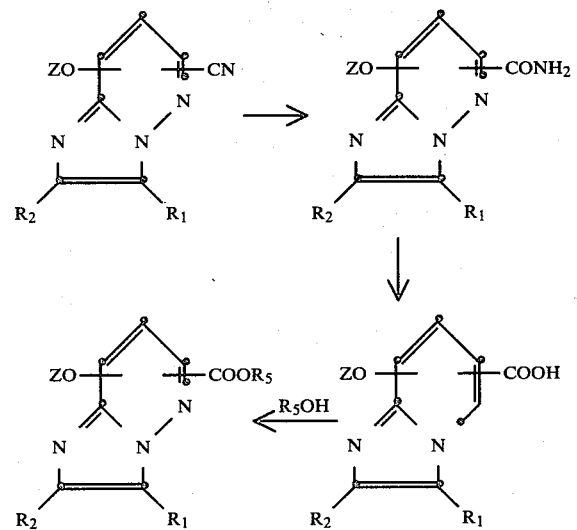

Sequence 2

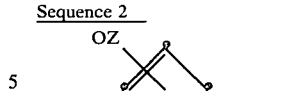

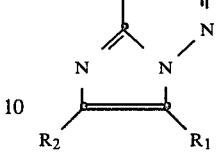

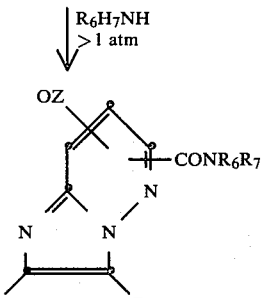

Sequence 3

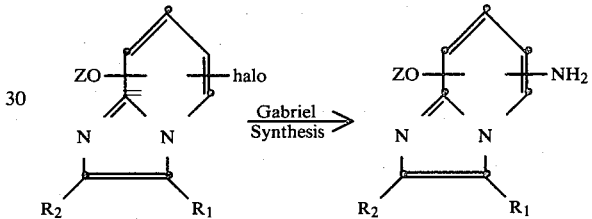

The imidazo compounds having an alkylsulfinyl or alkylsulfonyl substituent are prepared by oxidizing the corresponding $C_1$–$C_6$ alkylthio containing compound. Any suitable oxidizing agent, e.g. $H_2O_2$, may be used. The following equation illustrates the reaction

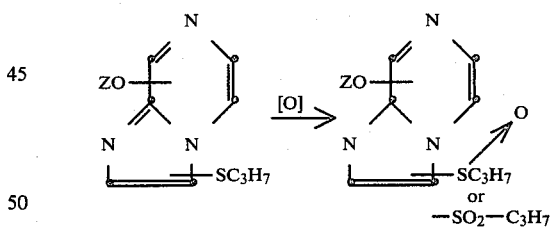

The compounds of the present invention have $\beta$-adrenergic blocking activity. This $\beta$-adrenergic blocking activity was determined by measuring the ability of representative imidazo compounds to block isoproterenol induced $\beta$-adrenergic stimulant effects such as heart rate increase, hypotension and bronchodilation, in an animal.

The observed $\beta$-adrenergic blocking activity of these imidazo compounds indicates that they are useful in humans which are benefited by $\beta$-blockade such as angina pectoris, arrhythmia etc.

Some imidazo compounds of the present invention also have antihypertensive activity of rapid onset. This antihypertensive activity is believed to be the result of peripheral vasodilation via a mechanism not directly related to the $\beta$-adrenergic blockade. Thus, these dual acting compounds provide an additional advantage over the ordinary β-adrenergic blocking agent by having immediate antihypertensive effect.

This rapid onset antihypertensive activity is determined by administering a representative imidazo compound to spontaneously hypertensive (SH) rats and measuring the effect on blood pressure. Representative compounds which were also found to have this antihypertensive activity are listed in the following table:

TABLE I

| Rapid Onset Antihypertensive Compounds | | | |
|---|---|---|---|
| Compounds Formula 1 | $R_1$ | $R_2$ | Administration Mode 2 |
| A | —SCF$_3$ | H | i.p.; p.o. |
| A | —CH$_3$ | CH$_3$ | i.p.; p.o. |
| A | —(CH$_2$)$_4$— | | i.p.; p.o. |
| B | H | H | i.p.; p.o. |
| A | Cl | H | i.p. |

1 Formula A is

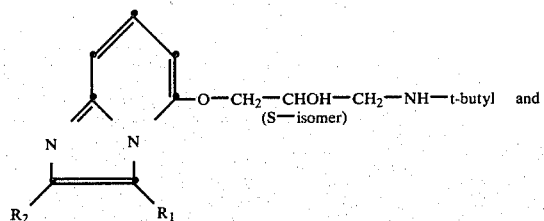

Formula B is

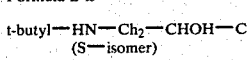

2 i.p. = intraperitoneal; p.o. = oral

For use as antihypertensives and/or β-adrenergic blocking agents, the compounds of the present invention can be administered orally or parenterally i.e. intravenously, intraperitioneally, etc. and in any suitable dosage form. The compounds may be offered in a form (1) for oral administration e.g. as tablets in combination with other compounding ingredients (diluents or carriers) customarily used such as talc, vegetable oils, polyols, benzyl alcohols, starches, gelatin and the like—or dissolved, dispersed or emulsified in a suitable liquid carrier—or in capsules or encapsulated in a suitable encapsulating material; or (2) for parenteral administration, dissolved, dispersed, or emulsified in a suitable liquid carrier or diluent. The ratio of active ingredients (present imidazo compound) to compound ingredients will vary as the dosage form requires. Conventional procedures are used to prepare the pharmaceutical formulations.

The daily dosage level for the present compounds as β-adrenergic blocking agents may be varied from about 0.01 mg. to about 100 mg. per kilogram of body weight. Daily doses ranging from about 0.01 to about 50 mg/kg. are preferred, with about 0.01 to about 1.25 mg/kg being a more preferred range. Oral administration is preferred.

The daily dosage level for the present compounds as antihypertensive agents may be varied from 1 mg/kg. to 50 mg/kg. A preferred daily dosage range is 1 to 25 mg/kg.

Either single or multiple daily doses may be administered depending on unit dosage.

The following examples illustrate the preparation of representative compounds of the present invention. All parts are by weight unless otherwise noted. All temperatures are °C.

Example 1 illustrates the preparation of intermediates used in preparing the imidazo compounds of the present invention.

EXAMPLE 1

(A)

3-Trifluoromethylthio-5-bromo-imidazo[1,2a]pyridine

A solution of 14.1 g. (0.072 mol.) of 5-bromo-imidazo[1,2a]pyridine in 90 ml. tetrahydrofuran is stirred at −10° C. under nitrogen and treated wth a steam of gaseous ClSCF$_3$ distilled from an ampoule. The mildly exothermic reaction is maintained 1 hour at −10°–0°, warmed cautiously at +10° and then room temperature, and filtered. The cake is recrystallized from absolute ethanol to give 4.0 g. white, solid hydrochloride of 3-trifluoromethylthio-5-bromo-imidazo[1,2a]pyridine compound, m.p. 205°–206° C.

The 3-trifluoromethylthio-5-bromo-imidazo[1,2a] pyridine base is obtained from the hydrochloride by extraction from aqueous sodium carbonate with CH$_2$Cl$_2$ and sublimation of the residue from evaporation of the extracts to give 1.5 g. crystals, m.p. 59°–60° C.

(B) 3,5-Dibromoimidazo[1,2a]pyridine

5-Bromoimidazo[1,2a]pyridine (6.0 g., 0.032 moles) is added to a solution of 6.0 g. (0.034 mol.) of N-bromosuccinimide in 50 ml. cold chloroform. After a mild exotherm the mixture is aged 2 hours at room temperature and then percolated through a column of 75 g. silica gel. The column is eluted with chloroform to give a light orange fraction which is concentrated in vacuo and the residue sublimed to give 6.25 g. 3,5-dibromoimidazo[1,2a]pyridine, m.p. 92°–94° C.

(C) 3-Chloro-5-bromoimidazo[1,2a]pyridine

A suspension of 5-bromoimidazo-[1,2a]pyridine (6.0 g., 0.031 mol.) and 5 g. N-chlorosuccinimide in 50 ml. carbon tetrachloride is heated to the boiling point for 20 minutes, cooled, and filtered. The filtrate is concentrated under vacuum to a dark solid which is dissolved in boiling ethanol. The ethanol solution is treated with charcoal, filtered, and the cooled filtrate chromatographed on 75 g. silica gel. The 3-chloro-5-bromoimidazo[1,2a] pyridine (4.5 g.) is eluted with chloroform and purified by sublimation, m.p. 99°–101° C.

(D) 3-Trifluoromethyl-5-bromoimidazo[1,2a]pyridine

To a stirred solution of 2-amino-6-bromopyridine (5.2, 0.030 mol.) in 50 ml 1,2-dimethoxyethane is added 11.3 g (0.06 mol) 1,1,1-trifluoro-3-bromo-2-propanone at room temperature. The mixture is stirred 18 hours and filtered to give 10.9 g. of 2-(1,1,1-trifluoro-2-keto-1-propaneamino)6-bromopyridine hydrobromide, m.p. 250° C. dec. This hydrobromide is dissolved in 25 ml. trifluoroacetic acid and the solution treated with 25 ml. trifluoroacetic anhydride. The mixture is stirred 3 hours at room temperature, concentrated under vacuum and the residual oil carefully neutralized with dilute aqueous sodium bicarbonate at ice temperature. The precipitated 3-trifluoromethyl-5-bromoimidazo[1,2a] pyridine (6.6 g.) is purified by sublimation, m.p. 130°–132° C.

(E) 2,3-Dimethyl-5-bromoimidazo[1,2a]pyridine

A mixture of 10.4 g. (0.060 mol.) of 6-bromo-2-aminopyridine and 9.0 g. (0.06 mol.) of 3-bromo-2-butanone in 40 ml. ethanol is refluxed 6 hours and then kept 18 hours at room temperature. The mixture is diluted with four volumes of ether to precipitate the hydrobromide of 2,3 dimethyl-5-bromoimidazo[1,2a]pyridine, 6.0 g., m.p. 270°–272° . The 2,3-dimethyl-5-bromoimidazo[1,2a]pyridine, 4.4 g., m.p. 69°–71°, is obtained by partitioning the crude hydrobromide between chloroform and aqueous sodium carbonate and sublimation of the CHCl$_3$ soluble material.

(F) 1-Bromo-6,7,8,9-tetrahydropyrido[1,2a]bnezimidazole .HBr

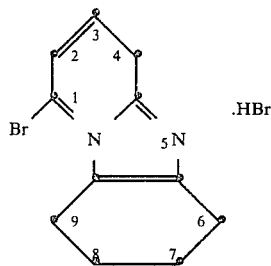

Similarly 2-chlorocylohexanone (4.0 g., 0.03 mol.) is reacted with 6-bromo-2-aminopyridine (5.2 g., 30 mmol.) in 30 ml. isopropanol for 18 hours at reflux to give 4.7 g. of white crystals of 1-bromo-6,7,8,9-tetrahydropyridoimidazo[1,2a]benzimidazole hydrobromide, m.p. 268°–269° C., after treatment with 4 ml. of 48% aqueous hydrobromic acid.

(G) 8-Phenyl-5-chloroimidazo[1,2a]pyridine

A mixture of 13 ml. of bromoacetaldehyde diethylacetal water (13 ml.) and 40% aqueous hydrobromic acid is refluxed vigorously for 1.5 hours, cooled, diluted to 300 ml. with 1,2-dimethoxyethane and treated with 33 g. of sodium bicarbonate. After carbon dioxide evolution ceases the mixture is filtered and the filtrate treated with 12.2 g. (0.0595 moles) of 6-chloro-3-phenyl-2-aminopyridine. The resulting mixture is refluxed for 16 hours, concentrated under vacuum and the residue dissolved in 50 ml. trifluoroacetic acid. The dark solution is treated with 20 ml. trifluoroacetic anhydride and stirred 3 hours at room temperature following the exotherm. The mixture is concentrated under vacuum and the residue is partitioned between ethyl acetate and aqueous sodium carbonate. The ethyl acetate extract is dried over sodium sulfate, filtered and concentrated under vacuum to an oil which is treated with 10 ml. of 40% aqueous hydrobromic acid in 100 ml. isopropanol. The crystallized hydrobromide of 8-phenyl-5-chloroimidazo[1,2a]pyridine, 11.0 g., m.p. 243°–245° C. is converted to 8-phenyl-5-chloroimidazo[1,2a]pyridine as Step A.), for example, and 8-phenyl-5-chloroimidazo[1,2a]pyridine purified, by recrystallization from hexane, 8.4 g., m.p. 66°–68° C.

(H) 8-Hydroxyimidazo[1,2a]pyridine

A solution of bromoacetaldehyde in 200 ml. absolute ethanol prepared from 20 g. of the diethylacetal as in Step G.) is treated with 7.1 g (0.065 mol.) of 2-amino-3-hydroxy pyridine and the mixture refluxed 3 hours, cooled, treated with styrenepolyamine ion-exchange resin until the solution is neutral and then filtered. The filtrate is concentrated to 75 ml under vacuum and 6.0 g. of 8-hydroxyimidazo[1,2a]pyridine, m.p. 175° C., collected by suction.

EXAMPLE 2

(A) S-8-3-tert. Butylamino-2-hydroxypropoxy)imidazo[1,2a]pyridine sesquioxalate hemihydrate A solution of S-2-phenyl-3-tert. butyl-5-hydroxymethyloxazolidine (8.8 g., 0.040 mol) is converted to 13.6 g. of its crude tosylate by treatment with 7.12 g. p-toluenesulfonylchloride in 14 ml. pyridine at 20°–30° for four hours, followed by benzene extraction from aqueous potassium carbonate.

8-Hydroxyimidazo[1,2a]pyridine (4.72 g., 0.035 mol.) is converted to its sodium salt with 1.48 g. of 50% NaH—mineral oil in 7 ml. N,N-dimethylformamide and the resulting solution is treated with said crude tosylate in 13 ml. N,N-dimethylformamide. The resulting mixture is heated to 100°–105° with stirring under nitrogen for 6 hours, quenched in ice water, and extracted with chloroform. The chloroform extracts are washed with water, extracted with 1.2 N aqueous hydrochloric acid and the aqueous acid extracts basified with sodium hydroxide and extracted with 1.2 N aqueous hydrochloric acid and the aqueous acid extracts basified with sodium hydroxide and extracted with ethyl acetate. The ethyl acetate extract is dried over sodium sulfate, concentrated and chromatographed on neutral alumina. S-8-(3-tert. Butylamino-2-hydroxypropoxy)imidazo[1,2a]pyridine, 1.2 g., is eluted with 1% methanol in chloroform and treated with a solution of 0.45 g. oxalic acid in hot ethanol. S-8-(3-tert. Butylamino-2-hydroxypropoxy)imidazo[1,2a]pyridine sesquioxalate hemihydrate, m.p. 157°–158°, crystallizes from the solution and is collected by suction.

(B) S-5-(3-tert. Butylamino-2-hydroxypropoxy)imidazo[1,2a]pyridine dihydrochloride A stirred suspension of 1 g. of about 50% by weight sodium hydride—mineral oil emulsion washed free of oil with hexane by decantation under nitrogen in 40 ml. N,N-dimethylformamide is treated with 4.71 g. (0.020 mol) of S-2-phenyl-3-tert. butyl-5-hydroxymethyloxazolidine and the mixture stirred at room temperature for 2 hours until hydrogen evolution ceases. The mixture is treated with 3.94 g. (0.020 mol.) of 5-bromoimidazo[1,2a]pyridine in portions. The mixture is stirred 1 hour at room temperature, quenched in ice water and extracted with ether. The combined ether extract is washed with water and extracted with two 12.5 ml. portions of 1.2 N aqueous hydrochloric acid. The combined aqueous acid extract is heated 30 minutes on the steam bath, extracted with benzene to remove benzaldehyde, basified with sodium hydroxide and the base of S-5-(3-tert. butylamino-2-hydroxypropoxy)imidazo[1,2a]pyridine dihydrochloride extracted with ethylacetate. The ethyl acetate extract is dried over sodium sulfate, filtered and concentrated under vacuum to an oil which is treated with 6 ml. ethanolic hydrogen chloride in 50 ml. isopropanol to give a dihydrochloride. Recrystallization from ethanol ether gives 3 g. of S-5-(3-tert. butylamino-2-hydroxypropoxy)imidazo[1,2a]pyridine dihydrochloride, m.p. 196°–197°.

Additional imidazopyridines of the present invention were prepared using the procedure of Example 2(B) but substituting the appropriate Example 1 intermediate for the 5-bromoimidazo[1,2a]pyridine reactant. The compounds and intermediates are tabulated below.

TABLE 2

Compounds of Formula A

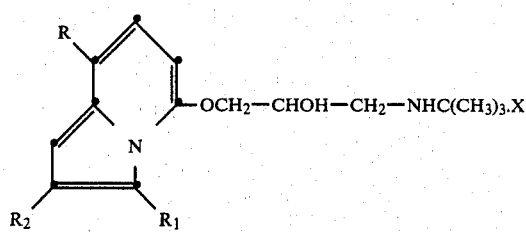

| Intermediate of Example 1 | Formula C Compound |  |  |  |  |
|---|---|---|---|---|---|
|  | R | $R_2$ | $R_1$ | $X^1$ | M.P. (°C.) |
| (A) | H | H | $SCF_3$ | Free Base | 135–6.5 |
| (B) | H | H | Br | $.2HCl.2H_2O$ | >350 |
| (C) | H | H | Cl | $.2HCl.\frac{1}{2}H_2O$ | 200 dec. |
| (D) | H | H | $CF_3$ | $.2HCl.H_2O$ | 147–48 |
| (E) | H | $CH_3$ | $CH_3$ | $.2HCl.\frac{1}{2}H_2O$ | 200–01 |
| (F) | H | $(CH_2)_4$ |  | Free Base | 154–55 |
| (G) | $C_2H_5$ | H | H | $.2HCl.H_2O$ | 185–87 |

[1] the salts, where indicated, were prepared by treating the free base with HCl in ethanol or ethanol-isopropanol.

EXAMPLE 3

S-8-(3-tert. Butylamino-2-hydroxypropoxy) imidazo[1,2a]pyrazine dihydrochloride hemihydrate Following the procedure of Example 2 B, 2.4 g. (0.01 mol), S-2-phenyl-3-tert. butyl-5-hydroxymethyloxazolidine is treated with 0.5 g. (0.01 mol) of a 50% by weight sodium hydride-mineral oil emulsin in 20 ml. N,N-dimethylformamide. To the resulting solution cooled to 0° is added 1.75 g. of a mixture of 8-chloro- and 8-bromoimidazo[1,2a]pyrazine (about 0.01 mol.) with stirring under nitrogen. Workup, after 18 hours at room temperature with aqueous 1.2 N hydrochloric acid, extraction of hydrolyzed benzaldehyde with benzene, basification with aqueous sodium hydroxide and extraction with chloroform, gives the free base of S-8-(3-tert. butylamino-2-hydroxypropoxy)-imidazo[1,2a]pyrazine dihydrochloride hemihydrate. The crude base is converted to the hydrogen maleate salt in acetonitrile and then to the hydrochloride via the free base by treatment with hydrogen chloride in isopropanol. The S-8-(3-tert. butylamino-2-hydroxypropoxy)imidazo[1,2a]pyrazine dihydrochloride hemihydrate, melts at 196°–197°.

EXAMPLE 4

S-5-(3-tert. Butylamino-2-hydroxypropoxy)-imidazo[1,2a]pyrazine dihydrochloride dihydrate Following the procedures of Example 2 B 3.07 g. (0.020 mol) of 5-chloroimidazo[1,2a]pyrazine is added to a solution of 1.0 g. 50% by weight sodium hydride-mineral oil emulsion (0.02 mol) and 4.70 g. (0.020 mol) of S-2-phenyl-3-tert. butyl-5-hydroxymethyloxazolidine in 40 ml. N,N-dimethylformamide with stirring at 0°–5° under nitrogen. Workup, after 1 hour at room temperature, with 1.2 N aqueous hydrochloric acid, extraction of hydrolyzed benzaldehyde with benzene, basification with aqueous sodium hydroxide, and extraction with chloroform gives the free base of S-5-(3-tert. butylamino-2-hydroxypropoxy) imidazo[1,2a]pyrazine dihydrochloride dihydrate. Treatment of the free base with hydrogen chloride in ethanol gives S-5-(3-tert. butylamino-2-hydroxypropoxy)imidazo[1,2a]pyrazine dihydrochloride dihydrate, m.p. 127°–129°.

Examples 5 and 6 illustrate the preparation of intermediates used in Examples 3 and 4.

EXAMPLE 5

5-Chloroimidazo[1,2a]pyrazine

A mixture of bromoacetaldehyde diethylacetal (13 ml.), water (13 ml.) and 40% aqueous hydrobromic acid (3.3 ml.) is refluxed 1.5 hours under nitrogen. The mixture is cooled, diluted with 300 ml. isopropanol, treated with sodium bicarbonate (33.3 g.) and filtered to give a solution of bromoacetaldehyde which is treated with 6-chloro-2-aminopyrazine (8.0 g., 0.062 mmol) at reflux for 18 hours under nitrogen. The mixture is concentrated to one-third volumn under vacuum and treated with 4 ml. 40% aqueous hydrobromic acid. The mixture is treated with fresh isopropanol and reconcentrated to give a crystalline hydrobromide salt of 5-chloroimidazo[1,2a]pyrazine, m.p. 300°. The crude salt is partitioned between aqueous sodium carbonate and chloroform and the chloroform extracts treated with charcoal, filtered through diatomaceous earth, and concentrated under vacuum. The crude 5-chloroimidazo[1,2a]pyrazine is sublimed to give 8.6 g. of yellow crystals, m.p. 95°–95.5°, of 5-chloroimidazo[1,2a]pyrazine.

EXAMPLE 6

8-Chloro and 8-bromoimidazo[1,2a]pyrazine

The procedure of Example 5 is repeated substituting 3-chloro-2-aminopyrazine and there is obtained a crude hydrobromide salt of 8-chloro and 8 bromoimidazo[1,2a]pyrazine mixture which is partitioned between aqueous sodium carbonate and chloroform. Concentration of the dried chloroform extracts and vacuum sublimation of the residue gives 8.3 g. of a mixture of 8-chloro and 8-bromoimidazo[1,2a]pyrazines, m.p. 176°–178°.

Claims to the invention follow.

What is claimed is:

1. A compound having the formula

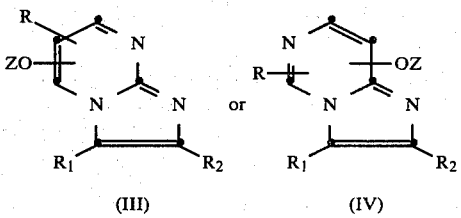

and pharmaceutically acceptable salts thereof wherein
Z is —$CH_2$—$CHOR_3$—$CH_2$—$NHR_4$ wherein $R_3$ is H or $C_2$–$C_{12}$ acyl and $R_4$ is $C_1$–$C_{12}$alkyl,
R is H, —$SCF_3$, —CN, halogen $C_{1-6}$alkyl, $NH_2$, $C_1$–$C_6$ haloalkyl, $C_1$–$C_{12}$acyl, phenyl
—$COOR_5$ wherein $R_5$ is H $C_1$–$C_6$alkyl or $C_6$–$C_{12}$ carbocyclic aryl,
—$CONR_6R_7$ wherein $R_6$ and $R_7$ when separate, are H or $C_1$–$C_6$alkyl and when joined, are —$CH_2$—$(CH_2)_3$—$CH_2$, —$CH_2$—$CH_2$—O—CH- $-CH_2-CH_2-$, $-CH_2-CH_2-NH-CH_2-CH_2-$, or $-CH_2-CH_2-N(CH_3)-CH_2-CH_2-$, $C_1-C_6$alkylthio, $C_1-C_6$ alkylsulfinyl or $C_1-C_6$alkylsulfonyl, and $R_1$ and $R_2$ when separate are R and when joined are $-(CH_2)_n$ wherein n is 3,4 or 5.

2. The compound of claim 1 wherein $R_3$ is hydrogen and $R_4$ is $C_3-C_4$ branched alkyl.

3. The compound of claim 2 wherein $R_1$ and $R_2$ are H, halogen, $C_1-C_6$alkyl, $C_1-C_6$acyl, $-SCF_3$ or $-(CH_2)_n$ wherein n is 3 or 4.

4. A compound of claim 3 wherein R is H, CN, phenyl or $CF_3$.

5. A compound of claim 4 wherein R is in the position ortho to the $-OZ$ group.

6. A compound of claim 4 having the S-isomer configuration.

7. A compound of claim 1 wherein Z is replaced by the oxazolidine group having the formula

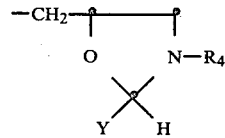

wherein $R_4$ is as defined in claim 1 and Y is H, $C_1-C_{12}$alkyl or $C_6-C_{12}$aryl.

* * * * *